United States Patent [19]
Curlee

[11] 4,178,922
[45] Dec. 18, 1979

[54] THERAPEUTIC BELT

[76] Inventor: James D. Curlee, 347 Rivermoor Dr., Marietta, Pa. 17547

[21] Appl. No.: 835,867

[22] Filed: Sep. 23, 1977

[51] Int. Cl.² .............................................. A61F 5/02
[52] U.S. Cl. ............................... 128/78; 128/DIG. 20
[58] Field of Search ................ 128/78, 89 R, DIG. 20

[56] References Cited

U.S. PATENT DOCUMENTS

| | | | |
|---|---|---|---|
| 1,646,590 | 10/1927 | Mildenberg | 128/DIG. 20 |
| 2,104,758 | 1/1938 | Poppen | 128/DIG. 20 |
| 2,240,308 | 4/1941 | Mahe | 128/DIG. 20 |
| 3,071,133 | 1/1963 | Eisen | 128/78 |
| 3,955,565 | 5/1976 | Johnson, Jr. | 128/89 R |

FOREIGN PATENT DOCUMENTS 985591  3/1965  United Kingdom ............ 128/DIG. 20

*Primary Examiner*—John D. Yasko
*Attorney, Agent, or Firm*—John S. Roberts, Jr.

[57] ABSTRACT

A therapeutic belt which is peculiarly adapted for the sacro-lumbar region of the body is disclosed. The belt appliance includes one or more inflatable cell structures integrally formed with the belt body as an extrusion. The inflatable structures are divided into air cell pockets by means of die cutting and heat sealing operations, and the pockets are fluidically connected to an air source by an air duct which is also integrally formed with the belt body and the inflatable cells. The pockets have different configurations and vary in size, and the extrusion is fabricated from a plastic vinyl material which exhibits a low coefficient of stretchability. The inflated configuration of the cell structure is also memorized into the material whereby substantially the same inflated configuration is always obtained. Precisely defined and located contact areas, developing predetermined amounts of counterpressure, are thus present within the appliance for application to the body portions for therapeutic purposes.

11 Claims, 16 Drawing Figures

THERAPEUTIC BELT

FIELD OF THE INVENTION

The present invention relates generally to therapeutic devices and more particularly to a therapeutic belt which may be worn about the sacro-lumbar region of the human body in order to prevent or treat injuries to the aforenoted body region.

BACKGROUND OF THE INVENTION

As is well known, the human spine or spinal column is comprised of seven cerivcal vertebrae, twelve thoracic vertebrae, and five lumbar vertebrae. The vertebrae are disposed in a stacked array and interposed between the same are fibrocartilages or discs. Thirty-one pairs of spinal nerves are also associated with the spinal column, and the nerves are sometimes adversely affected by means of the relative disposition of one or more vertebrae whereby severe pain results. For example, an accident, fall, uneven stress, tension, over-exertion, or the like, can cause a minor displacement or misalignment of one or more of the vertebrae which, in turn, can cause pressure to be exerted upon spinal nerve roots.

It has additionally been found that if the particular misaligned vertebrae is re-aligned in conjunction with the residual, properly aligned vertebrae, the pressure upon the spinal nerves is alleviated and, consequently, the pain suffered by the person is relieved. The re-alignment of the misaligned vertebrae is normally accomplished as a result of pressure being applied to the particularly afflicted areas of the body, and in accordance with these principles, prior art therapeutic appliances have been developed in order to provide such counter-pressure to the affected body regions.

Prior art appliances of the aforenoted type are exemplified by those disclosed in U.S. Pat. No. 3,071,133 issued to M. E. Eisen, and French Pat. No. 1,461,408 issued to M. Gross. The appliances include an inflatable bladder which seeks to exert the aforenoted counter-pressure upon the afflicted body portions as a result of the inflated expansion thereof; however, it has been found that such devices do not and cannot, in fact, exert the desired counter-pressure at the precise body location as required for the desired therapeutic purposes. This is particularly characteristic, for example, of appliances applied to the lumbar region of the body which, due to its peculiar curvature, usually does not receive adequate contact and pressurization from the appliance.

Still further, when such prior art appliances are normally employed, adequate contact and pressurization of the afflicted body region is attempted to be accomplished by means of increased tightening of the appliance about the wearer's body or increasing the degree of pressurization of the bladder. Such modes of practice are quite dangerous as other portions of the body are deleteriously affected. More particularly, as a result of the elastic properties of such bladder devices wherein the bladders have a high coefficient of stretchability, as the pressure within the bladders is increased, the contact area defined between the bladder and the body is increased and the cardio-vascular network of the body is severely constricted in a manner similar to that accomplished by means of a conventional blood pressure cuff. Prolonged usage of such appliances can therefore result in major complications, such as for example, renal ischemia, muscle spasms, arteriosclerosis-related problems, and even gangrene.

OBJECTS OF THE INVENTION

Accordingly, it is an object of the present invention to provide a new and improved therapeutic appliance.

Another object of the present invention is to provide a new and improved therapeutic appliance which is adapted to be applied to the lumbar region of the human back in order to relieve or prevent the occurrence of lower back pain afflictions.

Still another object of the present invention is to provide a new and improved therapeutic appliance for relieving or preventing the occurrence of pain within the sacro-lumbar region of the human back and which overcomes the various disadvantages characteristic of prior art appliances.

Yet another object of the present invention is to provide a new and improved therapeutic appliance which is adapted to be applied to the sacro-lumbar region of the human back in order to apply precisely localized counter-pressure to specific areas of the aforenoted back region.

Still yet another object of the present invention is to provide a new and improved therapeutic appliance which is adapted to be applied to the sacro-lumbar region of the human back and which is peculiarly capable of being accommodated within the aforenoted region which is characterized by a unique curvature.

A further object of the present invention is to provide a new and improved therapeutic appliance which employs a plurality of inflatable air cells wherein the configurations of the cells, the number of cells employed, and relative positions of the cells can be selectively varied so as to achieve optimum counter-pressure conditions.

A still further object of the present invention is to provide a new and improved therapeutic appliance which can be simply, easily, and economically manufactured by means of mass production techniques.

SUMMARY OF THE INVENTION

The foregoing and other objectives are achieved in accordance with the present invention through the provision of a therapeutic belt appliance which comprises one or more inflatable cell structures integrally formed with the belt body as an extrusion. The inflatable structures are divided into air cell pockets by means of die cutting and heat sealing operations, and the pockets are fluidically connected to an air source by means of an air duct which is also integrally formed with the belt body and the inflatable cells as a part of the extrusion. The pockets have different configurations and vary in size so as to provide precisely determined areas of contact to the body as the pockets are accommodated within, for example, the lumbar region of the body. The extrusion is also fabricated of a plastic vinyl material which exhibits a low coefficient of stretchability and, in addition, the inflated configuration of the cell is memorized into the material. Upon inflation of the cell structure, substantially the same configuration is always obtained whereby precisely located areas of counter-pressure may be developed and applied to the particular areas of the lumbar region of the body.

BRIEF DESCRIPTION OF THE DRAWINGS

Various other objects, features, and attendant advantages of the present invention will be more fully appreciated as the same becomes better understood from the following detailed description when considered in conjunction with the accompanying drawings, and wherein:

FIGS. 8A–11B are schematic views of further embodiments of the cell structures of FIG. 1.

DETAILED DESCRIPTION OF THE ILLUSTRATED EMBODIMENTS

Figure 1:
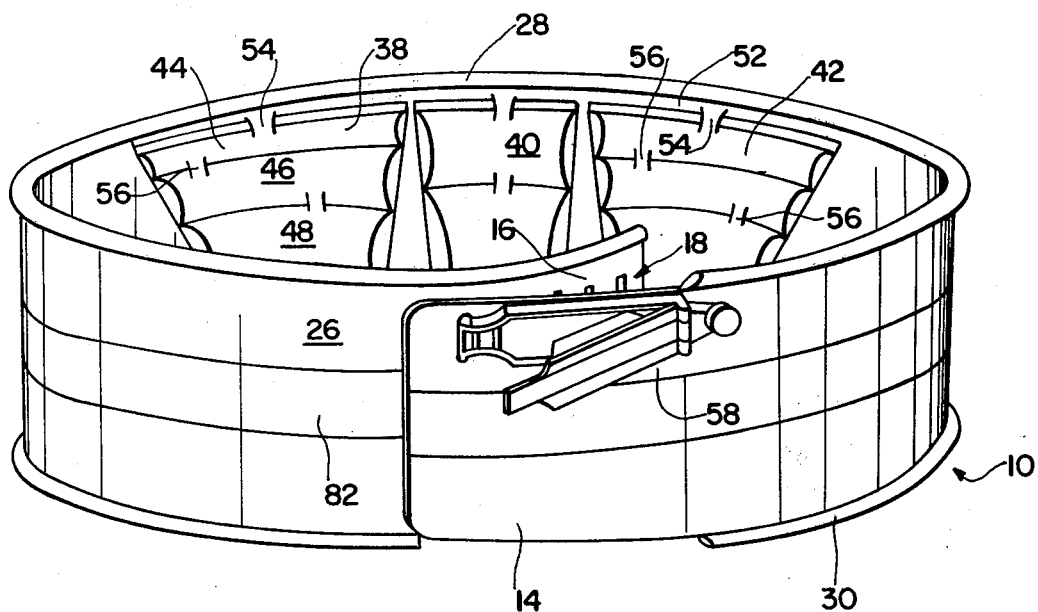
FIG. 1 is a perspective view of a belt appliance constructed in accordance with the present invention and showing its cooperative parts.
Figure 2:
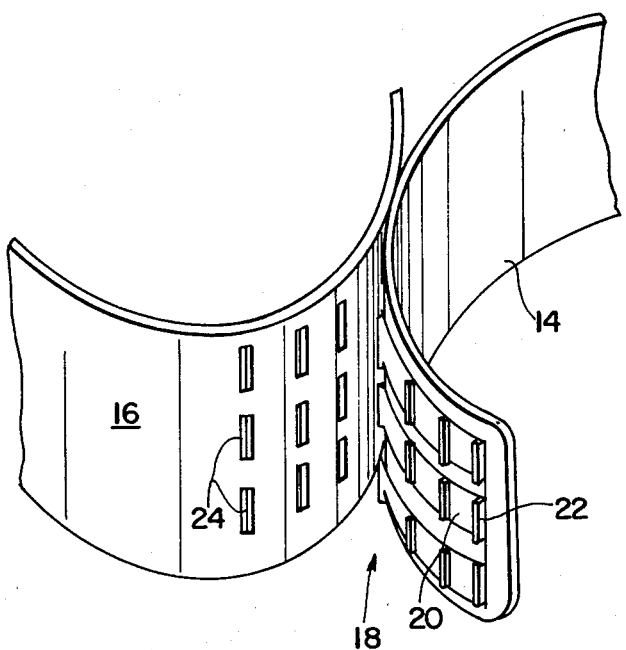
FIG. 2 is a partial perspective view of the fastening means of the belt of FIG. 1.
Figure 2A:
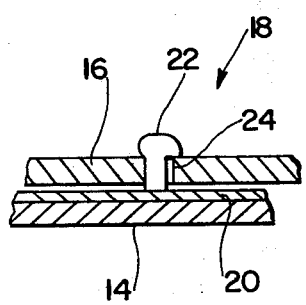
FIG. 2A is an enlarged detail view, in cross-section, of the fastening means of FIG. 2.

Referring now to the drawings and more particularly to FIG. 1 thereof, the therapeutic belt appliance of the present invention is generally indicated by the reference character 10. The belt is fabricated as an extrusion from suitable synthetic plastic, vinyl material and in order to secure the belt about the torso of the wearer, the free ends 14 and 16 of the belt are provided with suitable fastening means generally indicated by the reference character 18. As more particularly shown in FIG. 2, as well as the detailed view shown in FIG. 2A, the fastening means comprise a plurality of extruded nub bar bands 20 which may be heat-welded to the inner surface of belt end 14, each of the bands 20 having a plurality of crowned nub bars 22 longitudinally spaced thereon. Belt end 16 is similarly provided with a plurality of slotted apertures 24, which may be gang-punched therethrough, for matingly engaging the nub bars 22. As a result of the longitudinal array of the nub bars 22 and apertures 24, the belt is capable of being adjustably fitted to the torso of the particular wearer. In addition, it is also to be realized that other fastening means may be employed in lieu of the means 18, such as, for example, VELCRO, snap fasteners, or the like.

Figure 3:
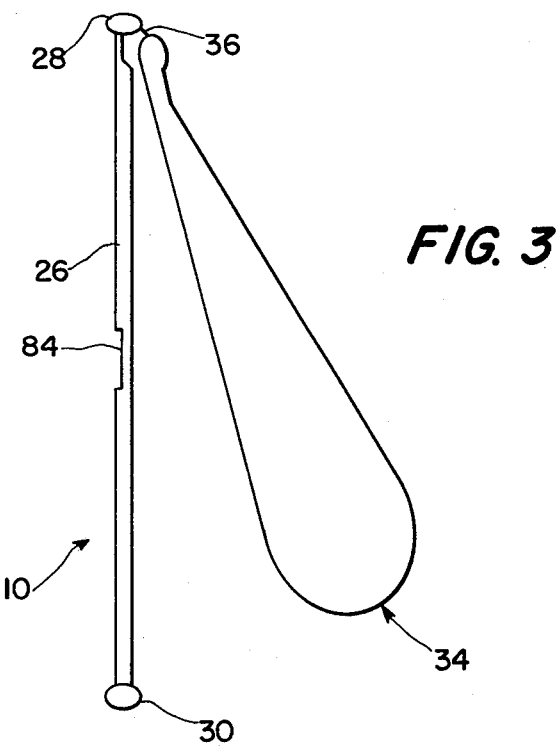
FIG. 3 is a cross-sectional view of the belt extrusion when initially extruded.

In fabricating the therapeutic belt of the present invention, the entire belt comprises a single extrusion, the cross-section of which has the configuration shown in FIG. 3. As shown, the belt body 26 comprises a substantially thick supporting band with the upper and lower edges thereof formed as hollow tubular structures 28 and 30, respectively. In this manner, when the belt 10 is applied to the torso of the wearer, the edge structures 28 and 30 serve as cushions which add a substantial degree of comfort to the wearer when the device is worn as the cushioned edges prevent chafing of the associated torso regions.

The inflatable air cell assemblies of the belt are fabricated from a tubular structure, generally indicated by the reference character 34, which is integrally connected to the upper belt body edging 28 by means of a connecting strip 36. In this manner, the air cell assemblies are dependently supported from belt body 26 and are adapted to be disposed interiorly of the belt body so as to be interposed between the belt 10 and the torso of the wearer. It will be realized that when the belt structure 10 is initially fabricated, as the extrusion for the same is a continuously extending structure which issues from the extrusion die, structures having particular lengths, corresponding to the desired lengths of belts 10, must initially be severed from the primary extrusion. In addition, it will also be realized that the length of the air cell tubular structure 34 is, at this time, the same as that of the belt body 26; however, this is undesirable as the cell assemblies are to be disposed only within the rear central portion of the belt 10.

Figure 4:
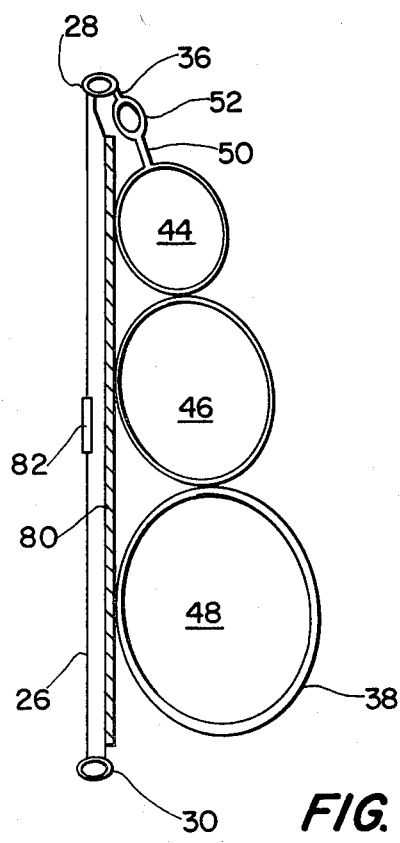
FIG. 4 is a cross-sectional view of the belt of FIG. 1.
Figure 5:
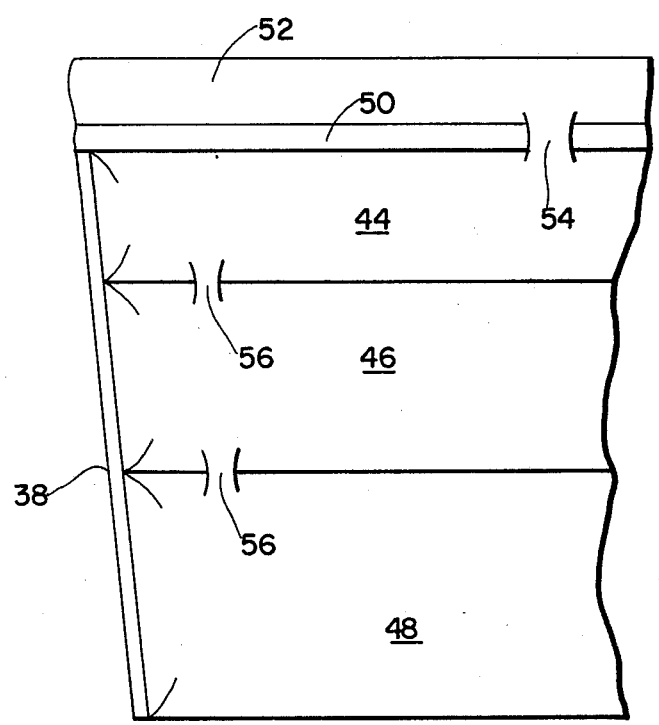
FIG. 5 is a partial front elevation view of the cell structure of FIG. 4.

Consequently, as can best be seen from FIG. 1, conventional rule dies may be utilized in order to sever and remove those portions of tubular structure 34 which extend laterally beyond the central portion of the structure 34 which will eventually define the cell assemblies. In addition, the rule dies are also utilized to sever the central portion of tubular structure 34 into, for example, three individual air cell assemblies 38, 40, and 42. Heat sealing dies are then utilized to seal the vertically extending sides of each of the individually formed air cell assemblies 38, 40, and 42 as well as to divide each of the assemblies 38, 40, and 42 into a plurality of air cell pockets 44, 46, and 48 as best seen in FIGS. 1, 4, and 5.

It will be noted that in forming the aforenoted air cell assemblies 38, 40, and 42, the uppermost portion of cell structure 34 is permitted to extend longitudinally about the belt 10 from the left side of cell assembly 38 to within the vicinity of belt end 14, as viewed in FIG. 1, and such portion of structure 34 is also separated from the cell assemblies 38, 40, and 42, as indicated at 50, by means of a heat sealing process in order to define an air transfer duct 52. Cross-ducts 54 are, of course, provided for fluidically interconnecting air transfer duct 52 to each of the cell assemblies 38, 40, and 42, and similar cross-ducts 56 are provided for fluidically interconnecting the individual pockets 44, 46, and 48 of the cell assemblies.

Figure 6:
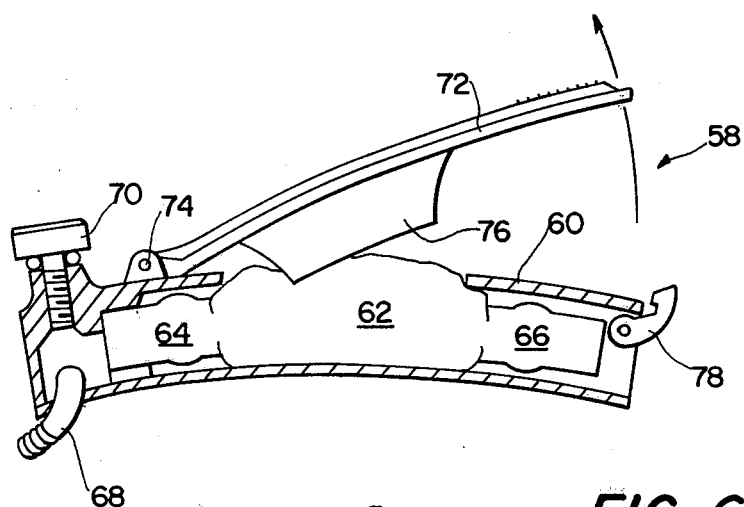
FIG. 6 is a cross-sectional view of the hand pump of the belt appliance of FIG. 1.

In order to provide for the inflation of the assemblies 38, 40, and 42, the end of the transfer duct 52 which terminates within the vicinity of belt end 14 is adapted to be operatively connected to an air pump device generally indicated by the reference character 58. As more particularly disclosed in FIG. 6, the air pump 58 is seen to comprise a housing 60 which is to be suitable secured to the other surface of belt body end 14 within the vicinity of the upper edging 28 and transfer duct 52. A compressible air cell 62 is disposed within housing 60, and the opposite ends of cell 62 are provided with one-way check valve assemblies 64 and 66. The outlet check valve 64 is fluidically connected with a tubular fitting 68 which is, in turn, fluidically connected to air transfer duct 62, and a relief valve 70 is also operatively associated with fitting 68 in order to relieve the pressurized air within the cell assemblies 38, 40, and 42 when deflation of the same is desired to be accomplished.

A pump handle 72 is pivotably secured to housing 60 by means of pivot pin structure 74, and it is seen that handle 72 includes an inwardly directed oblong projection 76 which operatively engages the compressible air cell 62 for accomplishing the inflation of the air cell assemblies 38, 40, and 42. A spring-biased latch mechanism 78 is also secured to housing 60 for operatively cooperating with handle 72 in permitting the same to be moved to its operative position or for retaining the same in its latched position during non-inflation periods.

Figure 7:
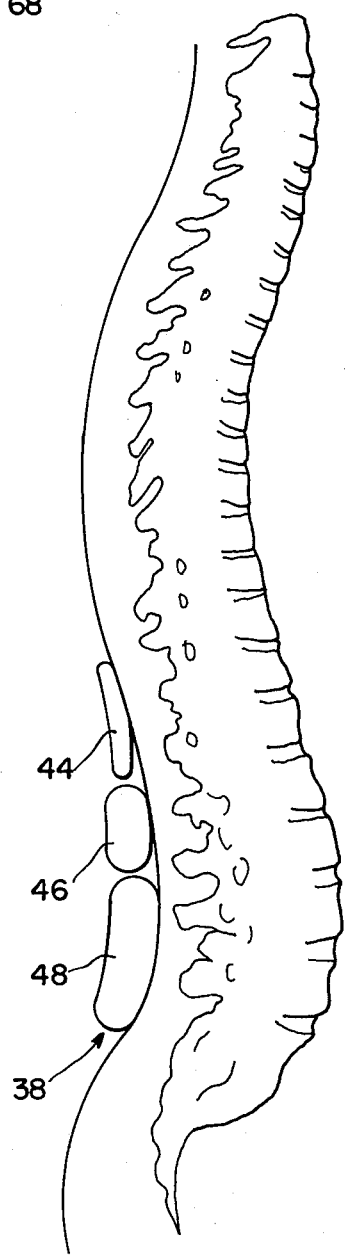
FIG. 7 is a schematic view showing the application of the belt structure to the sacro-lumbar region of the human body.
Figures 8A, 8B:
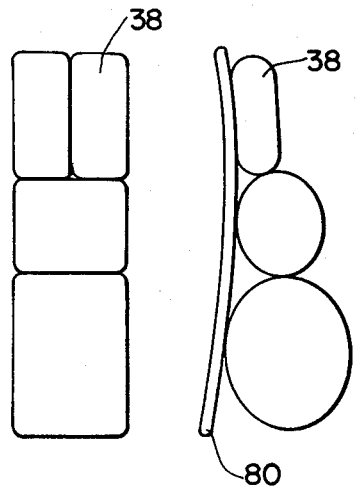
Figures 9A, 9B:
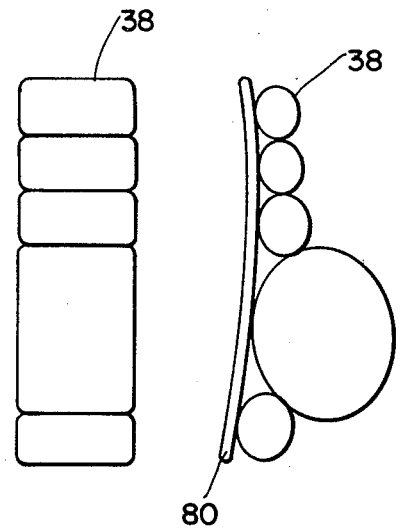
Figures 10A, 10B:
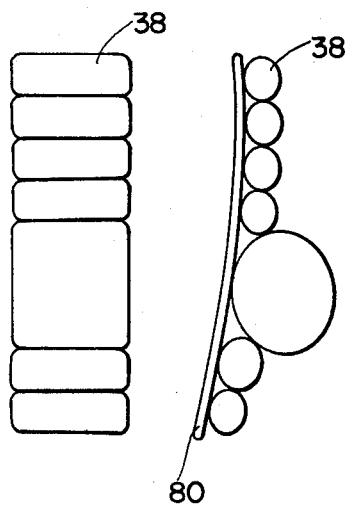
Figures 11A, 11B:
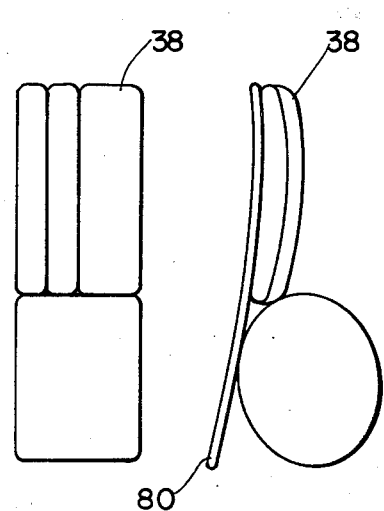

In utilizing the belt appliance of the present invention, the same is initially secured about the torso of the wearer with the fastening means 18 covering the abdominal area of the body while the inflatable cell assemblies 38, 40, and 42 are disposed within the lumbar region of the body as disclosed in FIG. 7. In conjunction with the belt body 26 and the cell assemblies 38, 40, and 42, a substantially rigid, plastic stay 80 is preferably interposed between body 26 and the cell assemblies, as shown in FIG. 4, in order to provide a predetermined amount of rigidity to the appliance as well as to maintain the cell assemblies properly positioned against the desired portions of the lumbar region in order to, in fact, apply the required counter-pressures thereto.

The synthetic plastic, vinyl material from which the appliance of the present invention is fabricated has unique inflation characteristics due to the fact that the material exhibits a low coefficient of stretchability, and the inflated configuration of the cell is memorized into the cell structure. Consequently, when the cell structure is deflated, the same assumes a substantially flattened state; however, when the cell structure is inflated, substantially the same cylindrical configuration is always obtained. This configuration is also substantially retained regardless of the pressurized conditions within th cell structure or the external pressures applied thereto. As a result, precisely located counter-pressure points may be developed and applied to the lumbar region of the wearer for the designated therapeutic purposes.

More particularly, as may be appreciated from FIG. 7, the cell structures 38 are configured so as to be precisely accommodated within the uniquely curved lumbar region of the back, and it is a further characteristic of the present inventive belt that the contact area defined between the individual pockets 44, 46, and 48 and the back is relatively small and is dependent upon the degree of pressurization within the cell structure and pockets. Moreover, contrary to the pressurization characteristics of conventional bladders, as the pressurization of the cells 38 is increased, the contact area defined between the cell structures and the back area decreases and the counter-pressure exerted upon the back by means of the cell structures is correspondingly increased. With conventional bladders, the contact areas increase with corresponding increases in pressure, and severe constriction of the cardio-vascular system results. Consequently, precisely controlled therapeutic results are obtained with the appliance of the present invention without concomitant dangerous effects being imposed upon the wearer's body and its vital systems.

While particularly configured cell structures have been disclosed, for example, within FIGS. 1, 4, 5, and 7 as comprising cell pockets 44, 46, and 48, it is also to be appreciated that, depending upon the particular type of therapy sought to be accomplished by means of the appliance of the present invention, various other cell structures and pocket configurations are, of course, possible. As shown, for example, in FIGS. 8A–11B, differently configured pockets may be fabricated by simply altering the heat sealing procedure described hereinabove. As a result of such altered processing, vertically and horizontally disposed pockets may be formed within the cell structures 38 as desired.

Still further, while three cell structures 38, 40, and 42 have been disclosed, for example, in FIG. 1 as being utilized within the appliance 10, a greater or smaller number of such structures may likewise be employed, the particular number again being dictated by the particular therapy sought to be accomplished. It is noted, for example, that with the appliance disclosed in FIG. 1, counter-pressure is developed upon both sides of the spinal column by means of structures 38 and 42, while additional counter-pressure is developed by means of structure 40 so as to act directly upon the spinal column.

Thus, it may be seen that the appliance of the present invention has important advantages over known prior art devices in view of the fact that precisely located areas of counter-pressure are in fact able to be developed and defined with respect to particular regions of the body in order to impart therapy thereto. In addition, as the belt appliance may be simply manufactured utilizing mass production extrusion, die cutting, and heat sealing techniques, selectively desired appliances may be economically produced as dictated by particular types of therapy required. In order to render the appliances acceptable for wardrobe coordination purposes, the outer body portion 26 may additionally be provided with one or more colored trim strips or bands 82 which are seated within corresponding configured recesses 84 formed within the belt body 26 as a result of the initial extrusion thereof.

Obviously, additional modifications and variations of the present invention are possible in light of the above teachings. It is therefore to be understood that within the scope of the appended claims the present invention may be practiced otherwise than as specifically described herein.

What is new and desired to be secured by Letters Patent of the United States is:

1. A therapeutic belt for application to the sacro-lumbar region of the human body comprising:
   a one-piece synthetic plastic body encircling member having free ends;
   cooperating releasable connecting means at said free ends for securing said body in position about a human torso;
   said body including a supporting band structure having upper and lower edge portions and of sufficient thickness to retain its body encircling relationship;
   a connecting strip of the same material as, but thinner than, said band structure and extending downwardly from said upper edge portion on the inner side thereof;
   and a plurality of inflatable air cell assemblies of the same material as said band structure and connecting strip and integral with and depending from said connecting strip.

2. A therapeutic belt as claimed in claim 1 in which said air cell assemblies comprise at least two laterally spaced air cell assemblies.

3. A therapeutic belt as claimed in claim 2 in which each air cell assembly includes a plurality of intercommunicating air-holding pockets.

4. A therapeutic belt as claimed in claim 3 in which said air-holding pockets are differently sized and configured so as to apply precisely located counter pressure to selected particular areas of the lumbar region of the body.

5. A therapeutic device as claimed in claim 4 and said air cell assemblies including a tubular air-supplying conduit depending from said connecting strip above said pockets and in air communication therewith; an air pump assembly carried by said hand structure; and air transfer means extending between said air pump assembly and said tubular air-supplying conduit said air cell assemblies whereby said air cell assemblies can be inflated.

6. A therapeutic belt as claimed in claim 5, and a hollow tubular means of the same material as said body member and constututing said upper and lower edge portions of said band structure so as to render said belt comfortable when secured to a human body.

7. A therapeutic belt as claimed in claim 6 and a rigid stay means interposed between said band structure and said air cell assemblies.

8. A therapeutic belt for application to the sacro-lumbar region of the human body comprising:
- a one-piece synthetic plastic body encircling member having free ends;
- releasable connecting means at said free ends for securing said body encircling member in position around a human torso;
- said body encircling member including laterally displaced inflatable air cell integral assemblies on the side thereof facing the sacro-lumbar region when in position around such a human torso; and
- said body member also including integral air-supplying conduit means in communication with said air cell assemblies.

9. A therapeutic belt as claimed in claim 8 further including an air pump assembly carried by said body encircling member; and air transfer means extending between said air pump assembly and said air-supplying conduit means whereby said air cell means can be inflated.

10. A therapeutic belt as claimed in claim 9 in which each air cell assembly includes a plurality of intercommunicating differently sized and configured air-holding pockets so as to apply precisely located counter pressure to selected particular areas of the lumbar region of the human body.

11. A therapeutic belt as claimed in claim 10 in which said synthetic plastic body encircling member is comprised of a vinyl material having a low coefficient of stretchability whereby the inflated condition of said air-holding pockets is memorized into the material thereof.

* * * * *